(12) United States Patent
Li et al.

(10) Patent No.: US 8,340,915 B2
(45) Date of Patent: Dec. 25, 2012

(54) SYSTEMS AND METHODS FOR ANALYZING MICROARRAYS

(75) Inventors: Lei M. Li, Los Angeles, CA (US); Chao Cheng, Los Angeles, CA (US); Huanying Ge, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 979 days.

(21) Appl. No.: 11/866,964

(22) Filed: Oct. 3, 2007

(65) Prior Publication Data

US 2008/0319679 A1    Dec. 25, 2008

Related U.S. Application Data

(60) Provisional application No. 60/828,029, filed on Oct. 3, 2006.

(51) Int. Cl.
*G01N 33/50* (2006.01)
*G01N 33/48* (2006.01)

(52) U.S. Cl. ........................................ 702/19
(58) Field of Classification Search ............... None
See application file for complete search history.

(56) References Cited

U.S. PATENT DOCUMENTS

2003/0139886 A1 *  7/2003  Bodzin et al. .................. 702/28

OTHER PUBLICATIONS

Cheng et al. (Sub-array normalization subject to differentiation, Oct. 4, 2005, Nucleic Acids Research, vol. 33, No. 17, pp. 5565-5573).*
B.M. Bolstad, et al. *A Comparison of Normalization Methods for High Density Oligonuceotide Array Data Based on Variance and Bias* [Bioinformatics Oxford University Press [vol. 19 No. 2 (2003) pp. 185-193].
Christopher Workman, et al. *A New Non-Linear Normalization Method for Reducing Variability In DNA Microarray Experiments* [Genome Biology (2002) vol. 3, No. 9].
Rafael A. Irizarry, et al. *Exploration, Normalization, and Summaries of High Density Oligonucleotide Array Probe Level Data*, [Biostatistics (2003),vol. 4, 2, pp. 249-264].
Wolfgang Enard, et al. *Intra- and Interspecific Variation In Primate Gene Expression Patterns* [Science, Apr. 2002, vol. 296, pp. 340-343].
I.A. Sidorov, et al. *Oligonucleotide Microarray Data Distribution and Normalization* [Information Sciences 146 (2002) pp. 67-73].

* cited by examiner

*Primary Examiner* — Jason Sims
(74) *Attorney, Agent, or Firm* — DLA Piper LLP (US)

(57) ABSTRACT

The present invention discloses methods and systems for analyzing microarray data. The method includes the general steps of providing microarray data, normalizing the data using a least trimmed squares regression, and then analyzing the normalized microarray data to obtain a desired result such as an expression profile. There is also disclosed a method of subdividing an array into subarrays before normalization. This approach provides a method for improving measurement accuracy and salvaging array data from arrays containing minor defects. Also disclosed is a Probe-Treatment-Reference (PTR) model for streamlining normalization and summarization of microarray data by allowing multiple references. Other aspects of the present invention include computer systems and computer readable media encoding methods of the present invention.

17 Claims, 11 Drawing Sheets

SYSTEMS AND METHODS FOR ANALYZING MICROARRAYS

CROSS-REFERENCE TO RELATED APPLICATIONS

This application claims an invention which was disclosed in Provisional Application No. 60/828,029 filed Oct. 3, 2006, entitled "ACCURATE AND JUSTIFIABLE MODULE FOR ANALYZING AFFYMETRIX GENECHIP MEASUREMENT". The benefit under 35 USC §119(e) of the United States provisional application is hereby claimed.

STATEMENT REGARDING FEDERALLY SPONSORED RESEARCH AND DEVELOPMENT

The present invention is made, at least in part, with the support of NIH grant R01 GM75308-01. The government has certain rights in the invention.

FIELD OF THE INVENTION

The invention pertains to the field of microarray data analysis. More particularly, the invention relates to methods for analyzing microarray data and computer software and systems for performing the methods.

BACKGROUND OF THE INVENTION

DNA Microarrays are miniature arrays containing gene fragments that are either synthesized directly onto or spotted onto glass or other substrates. Thousands of genes may be represented in a single array. A typical gene expression microarray experiment involves the following steps: (1) Preparation of fluorescently labeled target from RNA isolated from the biological specimens; (2) Hybridization of the labeled target to the microarray; (3) Washing, staining, and scanning of the array; (4) Analysis of the scanned image; and (5) Generation of gene expression profiles (see FIG. 1).

Currently two main types of DNA microarrays are being widely used in biomedical applications: oligonucleotide (usually 25- to 70-mers) arrays and gene expression arrays containing PCR products prepared from cDNAs. In forming an array, oligonucleotides can be either prefabricated and spotted to the surface or directly synthesized on to the surface (in silico). For example, Affymetrix's popular GeneChip (Santa Clara, Calif.) are arrays fabricated by direct synthesis of oligonucleotides on the glass surface. Oligonucleotides, usually 25-mers, are directly synthesized onto a glass wafer by a combination of semiconductor-based photolithography and solid phase chemical synthesis technologies. Each array contains up to 900,000 different oligos and each oligo is present in millions of copies (FIG. 2). Since oligonucleotide probes are synthesized in known locations on the array, the hybridization patterns and signal intensities can be interpreted in terms of gene identity and relative expression levels.

Although in principle, microarray experiments have opened a gateway to vast amount of data at a relatively fast speed and low cost, in reality, there still remains a number of key technical issues that limits microarray experiments from reaching their full potential. In particular, because interpretation of microarray measurements requires computational methods to translate the digital images into corresponding concentration readings, the accuracy of an microarray experiment largely hinges on the capability of available image analysis methods to accurately translate image intensity values to true concentration values. Many factors are known to play a role in this translation process, including the physical construction of an array, the chemistry of the sample, and the optics of the array reader, just to name a few.

In general, measurement values obtained from each array will have a 'block effect' due to variation in RNA extraction, labeling, fluorescent detection, etc. Without statistical treatment, this block effect is confounded with real expression differentiation. The process of applying statistical treatment to reduce the block effect is defined as normalization. This process is usually done at the probe level. Several normalization methods for oligonucleotide arrays have been proposed and practiced. One approach uses lowess normalization to correct for non-central and nonlinear bias observed in M-A plots. Another class of approaches correct for the nonlinear bias seen in Q-Q plots. As Workman et al. and Bolstad et al. discussed in their papers (Workman et al. (2002), *Genome Biol.*, 3, 1-16; Bolstad et al., (2003), *Bioinformatics*, 19, 185-193, the entire contents of both articles are incorporated herein by reference), several assumptions must hold in the methods using quantiles. First, most genes are not differentially regulated; second, the number of up-regulated genes roughly equals the number of down-regulated genes; third, the above two assumptions hold across the signal-intensity range. These three assumptions are adopted by most normalization methods in use today. For the purpose of discussion, these three assumption will herein be referred to as the standard assumptions.

Unfortunately, the standard assumptions do not always hold true. Thus, current crop of normalization methods are all quite restrictive in their capabilities. Without a reliable and generally applicable method of normalizing array data, the validity of results obtained from microarray experiments will always require further validation. Therefore, there is still a need in the art for a better normalization method that are generally applicable.

Accordingly, it is one object of the present invention to provide improved methods for analyzing microarray data that is capable of handling experimental conditions beyond the standard assumptions.

It is also an objective of the present invention to provide a better framework for processing microarray data that integrates normalization and summarization of data, thereby, improving the efficiency of microarray analysis.

These and other objects of the present invention are achieved through the methods and systems of the present invention. The principles and exemplary embodiments of the present invention will now be described in detail below.

SUMMARY OF THE INVENTION

In one aspect, the present invention provides a method of analyzing microarray data, comprising the steps of: providing a set of microarray data; grouping the microarray data into reference data and target data; normalizing the microarray data by applying a least trimmed squares regression method or a symmetric variant thereof to determine parameters for a linear model that fits the data; and analyzing the normalized micro-array data to obtain a desired result.

In another aspect, the present invention also provides a method for analyzing microarray data, comprising the steps of: providing a set of microarray data; subdividing the microarray data into subarrays; normalizing the microarray data within each subarray; and analyzing the normalized data to obtain a desired result.

In yet another aspect, the present invention further provides a method for obtaining expression profiles from microarray experiments which streamlines normalization and summarization of data, comprising the steps of: providing a set of microarray data from duplicate microarrays wherein at least one microarray is treated with treatment sample and at least one microarray is treated with control sample; selecting a plurality of reference arrays from among the microarrays and a plurality of corresponding target arrays from among the remaining microarrays according to a design of the microarray experiment; applying a normalization procedure to each pair of reference and target micro-arrays; summarizing the expression value for each probe-set from normalized microarray and reference array data according to a probe-treatment-reference (PTR) model, and estimating the parameters in the PTR model by a Least Absolute Deviations approach, whereby the steps of normalization and summarization are streamlined.

In yet another aspect of the present invention, there is provided A method for detecting defective areas on a microarray, comprising: dividing the array into a plurality of subarrays; applying a normalization procedure comprising a least trimmed squares method or a symmetric variant thereof, wherein said least trimmed squares regression method or the symmetric variant thereof normalizes the microarray data by estimating parameters for a linear model and fitting the data to the model; and estimating the parameters of the linear models across the plurality of subarrays to detect subarrays that are defective.

In addition to providing the above mentioned methods, the present invention further provides computer systems for practicing the above mentioned methods as well as computer readable media encoding the methods.

Other aspects and advantages of the invention will be apparent from the following description and the appended claims.

DETAILED DESCRIPTION

Figure 1:
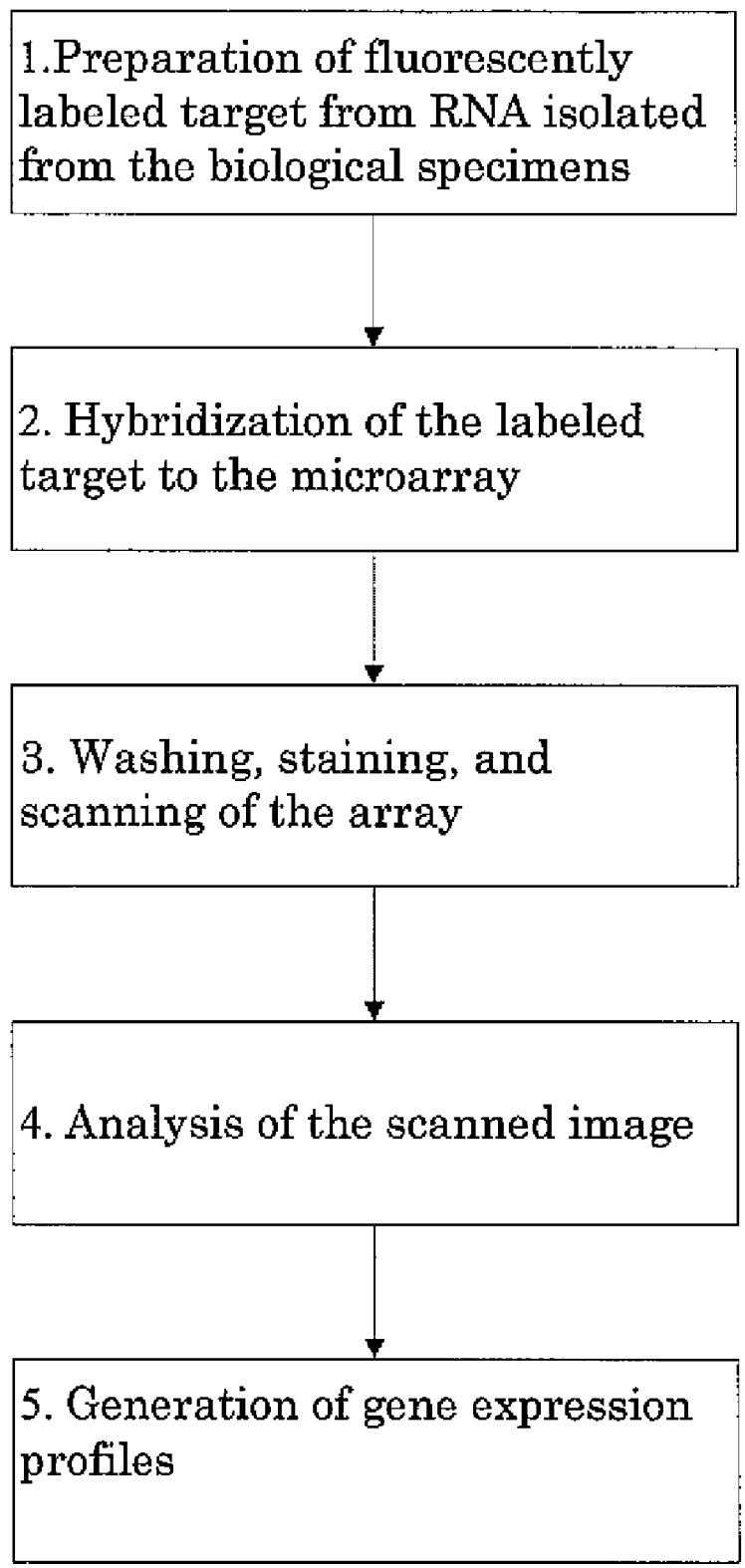
FIG. 1 shows a general workflow diagram for an exemplary microarray experiment.
Figure 2:
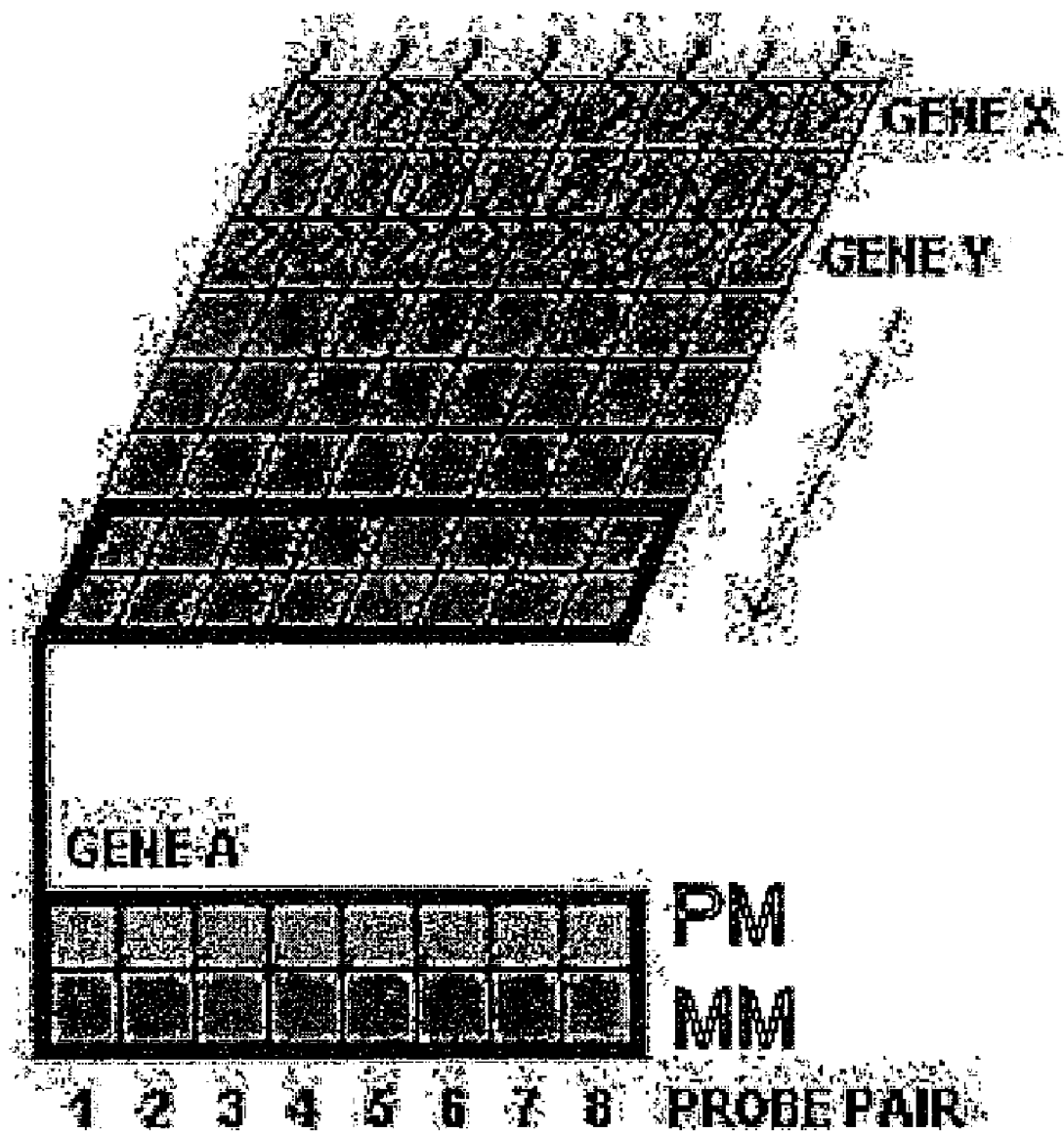
FIG. 2 shows an exemplary Affymetrix-type array. The Affymetrix-type array (termed GeneChip by Affymetrix) is made up of thousands of tiles with tethered nucleotides (tiles are sometimes, confusingly, called cells). A single gene is represented by adjacent tiles 16 to 24 times (i.e. each tile has tethered oligonucleotide), depending on the type of array (this serves as an internal repeat for each hybridization). For each of these tiles (oligonucleotide is a Perfect Match, PM—positive probe) there are the same number of adjacent tiles that are Mismatches (MM—negative probe). This therefore makes up a number of probe pairs. This serves as an internal control. The PMs and MMs for a single gene is collectively termed as a probe set.

To facilitate a full and complete understanding of the present invention, we will first begin with a brief discussion of the theoretical underpinnings of the methods and systems from which embodiments of the present invention are derived. However, it will be understood that the purpose of this discussion is only for illustration, and not to be interpreted as limiting in any way.

Overview

The problem of normalization can be conceptually understood as the need to compare apples to apples. For example, when comparing images taken from two separate arrays, the data from each array are biased differently due to the variability in the physical construction of the arrays and other factors. Thus, direct comparison of signals from the two arrays will amount to comparing apples to oranges. To overcome this problem, one must scale the signals from the two arrays to a common scale, or, in the microarray analysis jargon, data from the two arrays must be normalized before meaningful comparison can be carried out.

As mentioned in the background section, normalization is a major technical problem in microarray analysis. Many methods have been proposed in the art. However, existing methods can only deal with samples that differ from each other in a limited degree; large differences between two samples, especially asymmetric differences are not adequately addressed by existing methods. The inventors of the present invention have now formulated the normalization problem as a blind inversion problem. This formulation has the advantage of justifying the normalization results for various scenarios including those with little differentiation and those with substantial differentiation.

The basic concept of blind inversion is to use the information about the joint distribution of hybridization levels of the target and reference to find a transformation that can then be applied to transform the individual data points from observed values to true values. Two different ideas exist to achieve this goal. First, quantiles allows one to compare distributions. In this regard, the Q-Q plot is the standard graphical tool for the purpose. The normalization proposed in Sidorov et al. (*Inform. Sci.*, 146, 67-73 (2002), the entire content of which is incorporated herein by reference), Workman et al. (*Genome Biol.*, 3, 1-16, (2002)), and Bolstad et al., (*Bioinformatics*, 19, 185-193, (2003)) aims to match the marginal distribution of hybridization levels from the target with that from reference. Although slight and subtle difference exists between the two principles, quantile methods work well for arrays with little differentiation. The second idea is regression, either linear or nonlinear (Yang et al., *Microarrays: Optical Technologies and Informatics. SPIE* Vol. 4266; Schadt et al. *Cell. Biochem.*, 80, 192-202, (2000), the contents of both articles are incorporated herein by reference). The inventors have adopted the regression perspective in devising the methods of the present invention as it is easier to deal with the situations in which the standard assumptions are violated.

To illustrate exemplary methods of the present invention, we first consider the simple case of comparing two duplicate microarrays treated with different samples. When the two samples have largely different expression profiles, one needs to identify a 'base' subset for the purpose of normalization. This subset should exclude those probes corresponding to differentially expressed genes and abnormal probes due to experimental variation. Other methods known in the art generally adopt an 'invariant set' approach to choosing the base set. The invariant set can be a set of housing keeping genes that are known to express at the same level in different samples, or it may be identified by a ranking method that selects from the two samples a set of genes having the same ranking in their respective array data set. One can easily see that if the two datasets vary from each other greatly, the invariant set approach is ill equipped to handle such situations.

In the present invention, we propose a new approach to the identification of the base set and estimation of the transformation in a simultaneous fashion by adapting the least trimmed squares (LTS) algorithm (Rousseeuw, P. J. and Leroy, A. M. (1987) *Robust Regression and Outlier Detection*. Wiley, New York, the entire content of which is incorporated herein by reference). In this new approach, substantial differentiation is accommodated in LTS by setting an appropriate trimming fraction.

Another variability that may influence array normalization is the uncontrolled spatial variations in the arrays introduced during manufacturing or other random processes. There may also be array-specific spatial patterns due to uneven hybridization and measurement process. For example, reagent flow during the washing procedure after hybridization may be uneven; scanning may be non-uniform. We have observed different spatial patterns from one array to another. This problem is not well-recognized in the art. In the present invention, we explicitly take this spatial bias into consideration by divide each array into subarrays that consist of a few hundred probes and normalize probe intensities within each subarray. Other spatial normalization, such as that disclosed in Workman et al. (*Genome Biol.*, 3, 1-16. (2002)) only considers the spatial effect in background. In comparison, methods of the present invention are capable of adjusting for spatial differences both in background and in scale.

We now turn to the detailed conceptual formulation of the present invention.

Statistical Principle of Normalization

To illustrate the statistical principle underlying normalization, we consider the simple case of two arrays: one reference and one target. Denote the measured fluorescence intensities from the target and reference arrays by $(U_j, V_j)$. Denote true concentrations of specific binding molecules by $(\tilde{U}_j, \tilde{V}_j)$. Ideally, we expect that $(U_j, V_j) = (\tilde{U}_j, \tilde{V}_j)$. In practice, measurement bias exists due to uncontrolled factors and we need a normalization procedure to adjust measurement. Next, we have another look at normalization. Consider a system with $(\tilde{U}_j, \tilde{V}_j)$ as input and $(U_j, V_j)$ as output. Let $h = (h_1, h_2)$ be the system function that accounts for all uncontrolled biological and instrumental bias; namely, $$\begin{cases} U_j = h_1(\tilde{U}_j). \\ V_j = h_2(\tilde{V}_j). \end{cases}$$

The goal is to reconstruct the input variables $(\tilde{U}_j, \tilde{V}_j)$ based on the output variables $(U_j, V_j)$. Thus, in the present invention, the normalization problem is envisioned as a blind inversion problem, in which both input values and the effective system are unknown. As described above, the general idea of blind inversion is to find a transformation that matches the distributions of input and output. To do this, we must determine the joint distribution of true concentrations $(\tilde{U}_j, \tilde{V}_j)$. First, let us assume that the target and reference array are biologically undifferentiated. Under such condition, the differences between the target and reference are purely caused by random variation and uncontrolled factors. In this ideal case, it is reasonable to assume that the random variables $\{(\tilde{U}_j, \tilde{V}_j), j=1, \ldots\}$ are independent samples from a joint distribution $\tilde{\Psi}$ whose density centers around the straight line $\tilde{U} = \tilde{V}$, namely, $E(\tilde{V}|\tilde{U}) = \tilde{U}$. The average deviations from the straight line measure the accuracy of the experiment. If the effective measurement system $\hat{h}$ is not an identity one, then the distribution of the output, denoted by $\Psi$, could be different from $\tilde{\Psi}$. An appropriate estimate $\hat{h}$ of the transformation should satisfy the following: the distribution $\hat{h}^{-1}(\Psi)$ matches $\tilde{\Psi}$, which centers around the line $\tilde{V} = \tilde{U}$. In other words, the right transformation straightens out the distribution of $\Psi$.

Next we consider the estimation problem. Roughly speaking, only the component of $h_1$ relative to $h_2$ is estimable. Thus we let $v = h_2(\tilde{v}) = \tilde{v}$. In addition, we assume that $h_1$ is a monotone function. Denote the inverse of $h_1$ by g, then we expect the following is valid.

$E(\tilde{V}|\tilde{U}) = \tilde{U}$ or $E(\tilde{V}|g(U)) = g(U)$

PROPOSITION 1: Suppose the above equation is valid, then g is the minimizer of $\min_l E(V - l(U))^2$.

According to the well-known fact of conditional expectation, $E(\tilde{V}|g(U)) = g(U)$ minimizes $E(V - l_1(g(U))^2$ with respect to $l_1$. Next write $l_1(g(U)) = l(U)$. This fact suggests that we estimate g by minimizing $$\sum_j (V_j - g(U_j - 1))^2.$$

When necessary, we can impose smoothness on g by appropriate parametric or non-parametric forms.

Differentiation Fraction and Undifferentiated Probe Set

Next we consider a more complicated situation. Suppose that a proportion $\lambda$ of all the genes are differentially expressed while other genes are not except for random fluctuations. Consequently, the distribution of the input is a mixture of two components. One component consists of those undifferentiated genes, and its distribution is similar to $\tilde{\Psi}$. The other component consists of the differentially expressed genes and is denoted by $\tilde{\Gamma}$. Although it is difficult to know the form of $\tilde{\Gamma}$ a priori, its contribution to the input is at most $\lambda$. The distribution of the input variables $(\overline{U}_j, \overline{V}_j)$ is the mixture $(1-\lambda)\tilde{\Psi}+\lambda\tilde{\Gamma}$. Under the system function h, $\tilde{\Psi}$ and $\tilde{\Gamma}$ are transformed respectively into distributions denoted by $\Psi$ and $\Gamma$, i.e. $\Psi = h(\tilde{\Psi})$, $\Gamma = h(\tilde{\Gamma})$. This implies that the distribution of the output $(U_j, V_j)$ is $(1-\lambda)\Psi+\lambda\Gamma$. If we can separate the two components $\Psi$ and $\Gamma$, then the transformation h of some specific form could be estimated from the knowledge of $\tilde{\Psi}$ and $\Psi$.

Spatial Pattern and Sub-arrays

In the present invention, it is envisioned that normalization can be carried out in combination with a stratification strategy. For cDNA arrays, researchers have proposed to group spots according to the layout of array-printing so that data within each group share a more similar bias pattern. And then normalization is applied to each group. This is referred to as within-print-tip-group normalization. On a high-density oligonucleotide array, tens of thousands of probes are laid out on a chip. To take into account any plausible spatial variation in h, we divide each chip into sub-arrays, or small squares, and carry out normalization for probes within each subarray. To get over any boundary effect, we allow subarrays to overlap. A probe in overlapping regions gets multiple adjusted values from subarrays it belongs to, and we take their average.

Parameterization

Since each subarray contains only a few hundred probes, we choose to parameterize the function g by a simple linear function $\alpha+\beta u$, in which the background $\alpha$ and scale $\beta$ represent uncontrolled additive and multiplicative effects, respectively.

Simple Least Trimmed Squares

Our target solution consists of two parts: (i) identify the 'base' subset of probes; (ii) estimate the parameters in the linear model. We adopt LTS to solve the problem. Starting with a trimming fraction $\rho$, set $h=[n(1-\rho)]+1$. For any $(\alpha,\beta)$, define $r(\alpha,\beta)_i = v_i - (\alpha+\beta u_i)$; Let $H_{(\alpha,\beta)}$ be a size-h index set that satisfies the following property: $|r(\alpha,\beta)_i| \leq |r(\alpha,\beta)_j|$, for any $i \in H_{(\alpha,\beta)}$ and $j \notin H_{(\alpha,\beta)}$. Then the LTS estimate minimizes $$\sum_{i \in H_{(\alpha,\beta)}} r(\alpha,\beta)_i^2$$

The solution of LTS can be characterized by either the parameter $(\alpha,\beta)$ or the size-h index set H. It is this dual form that we find it ideal for our purpose. Statistically, LTS is a robust solution for regression problems. It has the advantage of being able to achieve any given breakdown value by setting a proper trimming fraction. It also has $\sqrt{n}$-consistency and asymptotic normality under some conditions. In addition, the LTS estimator is regression, scale, and affine equivariant.

An LTS solution naturally associates with a size-h index set. By setting a proper trimming fraction r, we expect the corresponding size-h set is a subset of the undifferentiated probes explained earlier. Obviously, the trimming fraction r should be larger than the differentiation fraction p.

Multiple Arrays and Multiple References

In the case of multiple arrays, the strategy of normalization hinges on the selection of reference. In some experiments, a master reference can be defined. For example, the time zero array can be set as a reference in a time course experiment. In experiments of comparing tumor and normal tissues, the normal sample can serve as a reference. In other cases, the median array or mean array are options for references. Another strategy is: first, randomly choose two arrays, one reference and one target, for normalization; use the normalized target array from the last normalization as the reference for the next normalization; iterate this procedure until all arrays have been normalized once; and repeat this loop for several runs. Prior art methods for summarizing multiple array experiments include the well-known median polishing algorithm in the RMA method (Irizarry et al., *Biostatistics*, 4, 249-264, (2003), the entire content of which is incorporated by reference). The quantile normalization method used in RMA can only deal with sample with little differentiation, and only use one reference, either a raw array or one synthesized from raw arrays. In the present invention, we further propose a method of summarizing multiple array experiments, the details of which are described in the next section.

The Probe-Treatment-Reference (PTR) Summarization Model

Thus far, we have established that the estimation of gene expression from probe intensities can be envisioned as a statistical problem. Current methods such as the method implemented in Affymetrix's MAS 5.0 software, the dChip software, and the RMA software all attempt to solve this problem by providing software consisting of two separate modules: one for normalization and one for summarization of data. Normalization aims to balance intensity values in order to reduce non-biological variations which are introduced during sample preparation and instrumental reading. Summarization combines normalized signal values in each probe-set and produces a final abundance estimate for the corresponding gene represented by the probe-set.

Normalization requires the specifications of reference and target arrays. One can normalize target arrays against a reference, no matter whether it is a raw microarray or an artificially-defined dataset. In the invariant-set normalization method, which is a part of the dChip software, the median intensity of each array is calculated, and the array with the median of these overall medians is chosen as the reference; however, other options are also allowed. The normalization is carried out according to the smooth curve fitted from the rank-invariant intensity set between the reference and target array. The quantile normalization in RMA uses complete data information and defines a pseudo-reference by the averaged quantiles. The normalization is carried out based on the quantile-quantile transformation. In the subarray normalization method of the present invention, once a reference and a target are given, it divides the whole array into sub-windows and normalizes probe intensities within each window using least trimmed squares (LTS) regression method. However, the issue of reference selection has not been well addressed.

In this invention, we propose a Probe-Treatment-Reference (PTR) method, which takes the reference-effect into account. The PTR method aims to streamline normalization and summarization by allowing multiple references. Instead of one reference array, it uses a reference set to do microarray pre-processing, namely, every array in this set serves as a reference for normalization. Compared to the two-factor model in the RAA, which contains probe- and array-specific effect (later we refer to it as the PA model), we reformulate the array-specific factor by a treatment factor and add a reference factor in the PTR model. In one exemplary embodiment, we implement the model by the least absolute deviations (LAD) approach, which has the advantage of being robust in the sense of the bounded influence (Bloomfield et al., *Least abso-*

*lute deviations: theory, applications, and algorithms.* Birkhauser 1983, the relevant portion of which is incorporated herein by reference).

The proposed PTR method is capable to integrate normalization with summarization in a unified framework. It can be applied to several existing normalization methods, and is particularly useful for the sub-array normalization which aims to reduce spatial variation. Because the reference-specific effect is adjusted at the probe-set level, implicitly, from the reference set, our model will define a "reference" for each probe-set, which may not come from the same raw array. The method has the advantage that the fold change estimates are resistant to a bad reference array. It reduces the variation of non-differentially expressed genes and thereby increases the detection power of differentially expressed genes.

Figure 6:
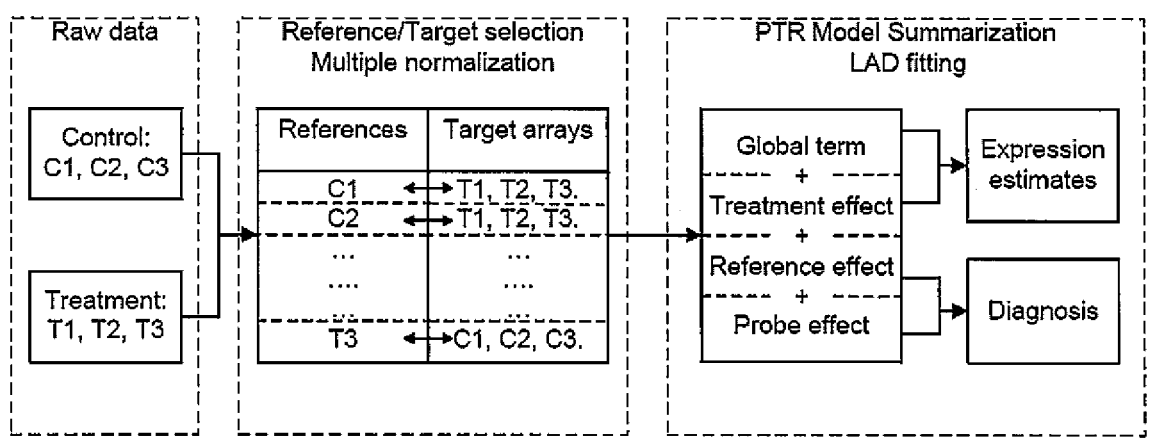
FIG. 6 shows a schematic representation of the PTR method.

The scheme of the PTR method is shown in FIG. 6. The PTR model fitting on is carried out on each probe-set. The inputs of the fitting are normalized results using multiple references. For the purpose of this discussion, we note that only PM probes are used even if the MM probes are available. Let variable $y_{ijkl}$ be the $j^{th}$ normalized probe intensity value of the $l^{th}$ replicate for the $i^{th}$ treatment, against the $k^{th}$ reference array, where $i=1\ldots,I; j=1,\ldots J; k=1,\ldots,K; l=1,\ldots,L$. We postulate that $\log_2(y_{ijkl})$ follows the three-factor model as below:

$$\log_2(y_{ijkl}) = \mu + \alpha_i + \beta_j + \gamma_k + \epsilon_{ijkl},$$

where $\mu$ is the global term; $\alpha_i$ represents the $i^{th}$ treatment; $\beta_j$ represents the $j^{th}$ probe-specific effect; and $\gamma_k$ represents the $k^{th}$ reference-specific effect. It is neither simple nor obvious to specify the distribution form for $\epsilon_{ijkl}$. In addition, they are correlated. In order to make the model identifiable, we can impose one of the following constraints:

Sum constraints:

$$\sum_i \alpha_i = 0, \sum_j \beta_j = 0, \sum_k \gamma_k = 0;$$

Median constraints: $\text{median}(\{\alpha_i\})=0, \text{median}(\{\beta_j\})=0, \text{median}(\{\gamma_k\})=0$ We use $\mu+\alpha_i$ for the final transcript abundance estimate for the $i^{th}$ treatment.

Suppose that we have two treatments and each has three replicates. The two-factor model has 22 (1+5+10) parameters, assuming the probe-set has 11 PM probes. After the model fitting, the expression value for each treatment usually will be calculated using the medians or means across the three replicates. The PTR model has 23 (1+1+10+5) parameters, if we include all six arrays in the reference set. The expression values for each treatment are calculated directly. Meanwhile, it does not necessarily lead to over-fitting if we use more reference arrays, since the number of normalized array increases accordingly. For example, using the cross strategy, three references generate 132 (4×11×3) normalized PM intensity values, while six references generate 264 (4×11×6) values.

Least Absolute Deviations (LAD) Estimation and its Computation

As described above, we have demonstrated an exemplary embodiment of the PTR model with LAD estimator implementation for estimating the parameters in the PTR model. That is, we minimize the sum of absolute errors (SAE):

$$SAE = \sum_{i,j,k,l} |\epsilon_{ijkl}| = \sum_{i,j,k,l} |\log_2(y_{ijkl}) - \mu - \alpha_i - \beta_j - \gamma_k|.$$

The LAD problem can be reformulated as a linear programming (LP) problem and thereby be solved via LP algorithms, such as the simplex and the interior point algorithm. However, in the PTR model, we notice that all regressors are categorical variables. It is easily seen that SAE is not minimized if the median of residuals indexed by the same level of any factor is not zero. in this case the corresponding $\alpha_i$, $\beta_j$ or $\gamma_k$ can be adjusted to make the median be zero and reduce the sum in the three-factor model equation. Therefore, the LAD solution has the property:

$$\begin{cases} \text{median}(\{\epsilon_{ijkl}\} \mid i) = 0, \\ \text{median}(\{\epsilon_{ijkl}\} \mid j) = 0, \\ \text{median}(\{\epsilon_{ijkl}\} \mid k) = 0. \end{cases}$$

Consequently, we can minimize the sum of absolute deviations by "median polish" approach. Namely, in each step, we sweep out the median for each level of one categorical variable. In each iteration, we run the median polishing through all categorical variables. The SAE is reduced during each step and we stop the iteration once it becomes stable. Our experiences show that at most 20 iterations give satisfactory results.

Strategy of Normalization and Summarization

To further illustrate the PTR method we describe here a typical treatment-control case where we have three replicates for control and three for treatment. First, we select multiple references and their target arrays. We propose two simple and straightforward strategies as follows.

The all-pairwise strategy: all arrays are included in the reference set; for each reference, all the other arrays are its targets.

The cross strategy: all arrays are included in the reference set; for each reference from control, we take replicates from treatment as its target arrays; conversely, for each reference from treatment, we take replicates from control as its target arrays.

Second, we may use existing normalization algorithms such as the invariant-set, sub-array and quantile, to do normalization between each reference and its target arrays. In one exemplary embodiment, we use the function normalize.AffyBatch.invariantset in the BioConductor's affy package to carry out the invariant-set normalization. We keep the default parameter settings but allow the reference to be selected manually. We also applied normalization method of the present invention for sub-array normalization. The window size is 25, the overlapping size is 10 and the trimming factor is 0.55 for the HG-U133A dataset. We may normalize each target array against a raw reference array as follows: sort the reference and the target array respectively in the ascending order; replace the sorted intensity values in each target array with those in the reference array; rearrange intensities in each target array to the original order.

Finally, for each probe-set, we summarize the arrays from log-transformed PM intensities according the three-factor PTR model: $\log_2$ (Intensity)=global term+treatment effect+probe effect+reference effect. The model states that the variation of logarithmic probe signal values could be sufficiently explained by treatments, probe affinities and references in normalization. The global term and treatment effects are taken to be the final transcript abundance estimates; the reference effect and the probe effect could be used for diagnosis.

Exemplary Embodiments

Having the benefit the above theoretical discussion, we now turn our attention to the exemplary embodiments of the present invention.

In one aspect, the present invention provides a method of analyzing microarray data, comprising the steps of: providing a set of microarray data; grouping the microarray data into reference data and target data; normalizing the microarray data by applying a least trimmed squares regression method or a symmetric variant thereof to determine parameters for a linear model that fits the data; and analyzing the normalized micro-array data to obtain a desired result.

In general, a person skilled in the relevant art will appreciate that a method according to the present invention is not limited to the analysis of microarray data, but is also applicable to any data analysis situations where normalization of replica dataset is required. For the purpose of discussion, analysis of microarrays are provided as exemplary embodiments.

The term "microarray" as used herein refers to a broad range of instrumentation and techniques that share the same characteristics of having a miniature footprint, and capable of a high degree of parallelism for high-throughput data generation. Exemplary microarrays include, but are not limited to oligonucleotide arrays (also known as Affymetrix-type arrays), cDNA arrays, bead arrays, pathway arrays, ChIP-chip experiments, methylation arrays, exon arrays, tissue arrays, and protein arrays.

In embodiments of the present invention, normalization is done using regressional analysis, preferably a least trimmed squares regression method or a symmetric variant thereof. Computation of least trimmed squares algorithm may be implemented by any means commonly known in the art. Preferably, a fast and stable computation algorithm computation previously introduced by the inventors is used (Li, L. M., *Comput. Stat. Data Anal.*, 48, 717-734, (2004), the entire content of which is incorporated herein by reference).

When analyzing data obtained from oligonucleotide arrays, methods of the present invention may further include the step of dividing the array into subarrays and normalizing the data within each subarray. Typically, all data from the probe-set are used, but alternatives such as excluding data from the mismatched probes may also be advantageous considered. The subarray may range from about 10×10 data points in size to about 100×100 data points. Adjacent subarrays may also be allowed to overlap each other. The portion of overlap may range from about 0% to any percentage less than 100%.

Often times, design of microarray experiment will call for duplicates. Hence, in some embodiments, methods of the present invention will take microarray data from a set of duplicate microarrays wherein at least one of the duplicate microarrays is treated with a reference sample and at least one of the duplicate microarrays is treated with a target sample.

One major advantage of normalizing data with a least trimmed squares method according to embodiments of the present invention is that one may set the trim fraction in accordance with the desired sensitivity and experimental design. The trim faction is preferably larger than the fraction of differentiated probes. This is important because the fraction used in regression should be within the fraction range of undifferentiated probes.

The concept of sub-dividing an array into subarrays for analysis is a useful tool in the analysis of data that are arranged in matrix format. Thus, in another aspect, the present invention can also be seen as providing a method for analyzing microarray data, comprising the steps of: providing a set of microarray data; subdividing the microarray data into subarrays; normalizing the microarray data within each subarray; and analyzing the normalized data to obtain a desired result A skilled person in the art will readily appreciate that the concept of subarray will also work with normalization techniques other than the least trimmed squares regression. However, the use of least trimmed squares regression is preferred.

After the array data are normalized, one may then proceed to analyze the data to obtain the desired outcome. Exemplary desired outcome may include time-series of gene expression profile, or any other information relevant to answering a biological question. Analysis and interpretation of the normalize array data will generally be determined by experimental design. To deal with the large number of data points generated, a number of statistic methods may be beneficially employed, which may include, but are not limited to estimation, testing, clustering, and discrimination.

In yet another aspect, the present invention further provides a method for obtaining expression profiles from microarray experiments which streamlines normalization and summarization of data, comprising the steps of: providing a set of microarray data from duplicate microarrays wherein at least one microarray is treated with treatment sample and at least one microarray is treated with control sample; selecting a plurality of reference arrays from among the microarrays and a plurality of corresponding target arrays from among the remaining microarrays according to a design of the microarray experiment; applying a normalization procedure to each pair of reference and target micro-arrays; summarizing the expression value for each probe-set from normalized microarray and reference array data according to a probe-treatment-reference (PTR) model, and estimating the parameters in the PTR model by a Least Absolute Deviations approach, whereby the steps of normalization and summarization are streamlined.

The arrays may be treated at multiple levels, or treated at a single level. In either case, the method is capable of accommodating both experimental designs.

In the PTR method, the key is the use of multiple references. In one embodiment, a reference selection strategy is adopted such that all microarrays are included in the reference set; and, for each reference, all the other microarrays are its targets. In another embodiment, reference and target arrays are selected such that all microarrays treated with control sample are included in the reference set, and for each reference that is treated with control sample, replicates from arrays treated with treatment sample are taken as its target arrays.

In yet another aspect of the present invention, there is provided a method for detecting defective areas on a microarray, comprising: dividing the array into a plurality of subarrays; applying a normalization procedure comprising a least trimmed squares method or a symmetric variant thereof, wherein said least trimmed squares regression method or the symmetric variant thereof normalizes the microarray data by estimating parameters for a linear model and fitting the data to the model; and estimating the parameters of the linear models across the plurality of subarrays to detect subarrays that are defective.

In addition to providing the above mentioned methods, the present invention further provides computer systems for practicing the above mentioned methods as well as computer readable media encoding the methods.

Figure 10:
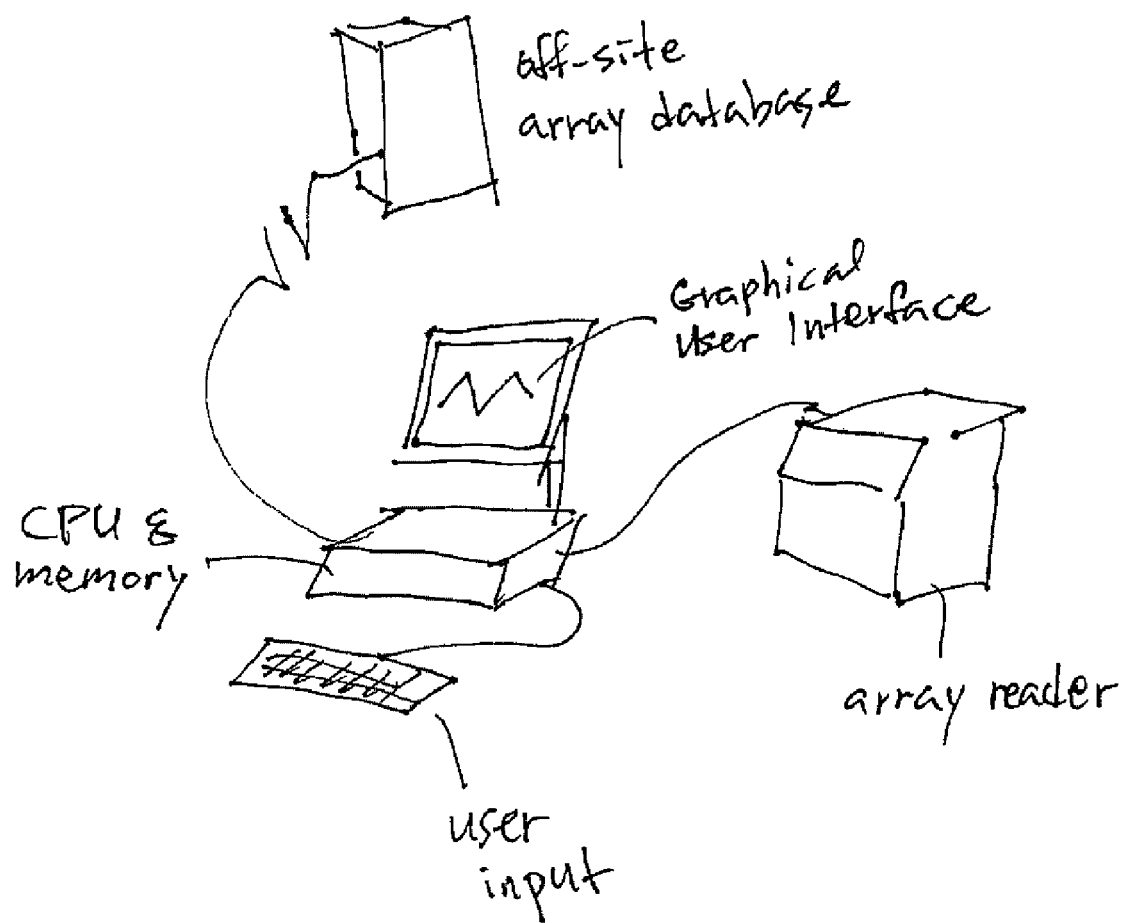
FIG. 10 shows an exemplary computer system according to one embodiment of the present invention.

In one embodiment, it is envisioned that the method is implemented to be executed by a computer as a stand-alone workstation. Computer implementation of the method may be achieve by any commonly used programming methodologies known in the art. Exemplary implementations may include C/C++, Fortran, Java, or the like. It is also envisioned that a microarray reader system may incorporate a computer system according to the present invention. In such a scenario, customized hardware and circuitry may be created to execute methods of the present invention at an increased speed than general purpose PC. Incorporating computer system of the present invention into a microarray reader system provides the advantage of convenience to the user. FIG. 10 shows an exemplary computer system of the present invention.

Other approaches of implementing the methods of the present invention are also contemplated. For example, a web-based application service model wherein instruction for directing a computer to execute the method is delivered in real-time over the network offer certain advantages and is contemplated in the present invention.

To further illustrate the methods and systems of the present invention, the following specific examples are provided.

EXAMPLES

Example 1

Microarray Data

The Affymetrix Spike-in dataset, which includes 14 arrays, was obtained from Affymetrix HG-U95 chips. Fourteen genes in these arrays were spiked-in at given concentrations in a cyclic fashion known as a Latin square design. The data are available from Affymetrix's website. In the examples described herein, eight arrays were chosen from the complete set and split into two groups. The first group contained four arrays: m99hpp_av06, 1521n99hpp_av06, 1521o99hpp_av06 and 1521p99hpp_av06. The second group contained four arrays: q99hpp_av06, 1521r99hpp_av06, 1521s99hpp_av06 and 1521t99hpp_av06. For the sake of brevity, these arrays will henceforth be designated by letters M, N, O, P, Q, R, S, and T. As a result, the concentrations of 13 spiked-in genes in the second group are 2-fold lower. The concentrations of the remaining spike-in genes are respectively 0 and 1024 in the two groups. In addition, two other genes are so controlled that their concentrations are also 2-fold lower in the second group compared with the first one.

From the same Affymetrix webpage, two replicates using yeast array YG-S98 were also available: Yeast-2-121501 and Yeast-2-121502. These data were used to study the variation between array replicates.

Expression profiles offer a way to study the difference between humans and their closest evolutionary relatives. We consider the publicly available dataset from Enard et al., (*Science*, 296, 340-343, (2002), the entire content of which is incorporated herein by reference). Two brain samples were extracted from each of three humans, three chimpanzee and one orangutan. In what follows we only show results on two human individuals, HUMAN 1 and HUMAN 2, one chimpanzee, CHIMP. 1 and the orangutan, ORANG. The mRNA expression levels were measured by hybridizing them with the Affymetrix human chip HG-U95.

Implementation and SUB-SUB Normalization

We have developed a module to implement the normalization method described above, referred as SUB-SUB normalization. The core code is written in C, and we have interfaces with Bioconductor in R. The input of this program is a set of Affymetrix CEL files and outputs are their CEL files after normalization. Three parameters need to be specified: subarray size, overlapping size and trimming fraction. The sub-array size specified the size of the sliding window. The overlapping size controls the smoothness of window-sliding. Trimming fraction specifies the breakdown value in LTS. An experiment with an expected higher differentiation fraction should be normalized with a higher trimming fraction.

Parameter Selection

We have tried many combinations of the three parameters on several datasets. In some reasonable range, the interaction between the parameters is negligible. In general, the smaller the sub-array size is, the more accurately we can capture spatial bias while the less number of probes are left for estimation. Thus, we need to trade off bias and variation. From our experiments, we recommend 20·20 for Affymetrix HG-U95 and HG-U133 chips. The value of overlapping size is the same for both directions, and we found its effect on normalization is the least among the three parameters. Our recommendation is half of the sub-array size. For example, it is 10 if sub-array size is 20·20. According to our experience, it can even be set to 0 (no overlapping between adjacent sub-arrays) to speed up computation without obvious change to normalization. The selection of trimming fraction should depend on samples to be compared in the experiments and quality of microarray data. For an experiment with 20% differentiated genes, we should set a trimming fraction >20%. Again we need a trade off between robustness and accuracy in the selection of trimming fraction. On the one hand, to avoid breakdown of LTS, we prefer large trimming fractions. On the other hand, we want to keep as many probes as possible to achieve accurate estimates of a and b. Without any a priori, we can try different trimming fractions and look for a stable solution. Our recommendation for starting value is 50%.

Affymetrix Spike-in Dataset

Figure 3:
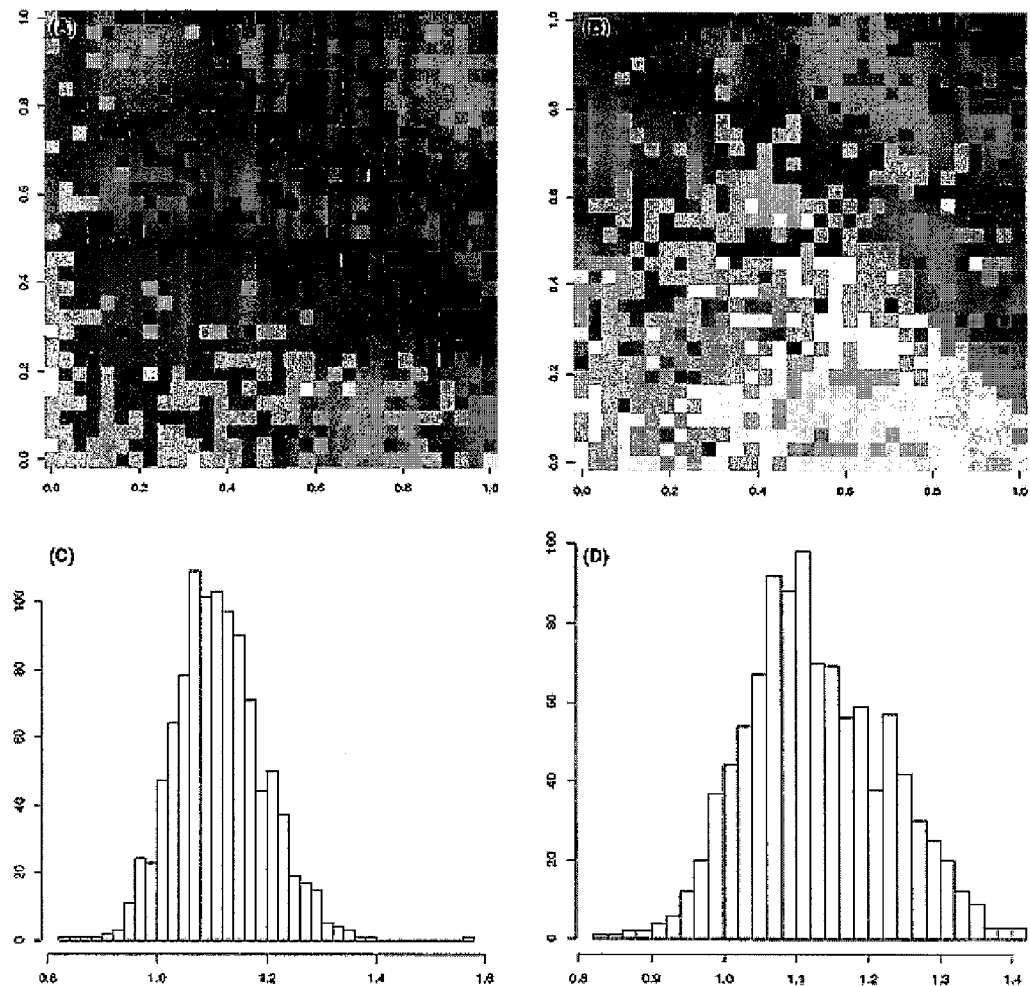
FIG. 3 shows the slope matrices of two arrays which illustrate different spatial patterns in scale. The common reference is Array M. (A) Array P versus M; (B) Array N versus M. (C and D) Their histograms are shown at bottom correspondingly.

We first investigate the existence of spatial pattern. The HGU95 chip has 640×640 spots on each array. We divided each array into sub-arrays of size 20×20. We run simple LTS regression on the target with respect to the reference for each sub-array. This results in an intercept matrix and a slope matrix of size 32·32, representing the spatial difference between target and reference in background and scale. We first take Array M as the common reference. The slope matrices of Array P and M are shown in FIGS. 3A and B, respectively, and their histograms are shown in FIGS. 3C and D. Two quite different patterns are observed. Similar phenomenon. exists in patterns of $\alpha$. The key observation is that spatial patterns are array-specific and unpredictable to a great extent. This justifies the need of adaptive normalization.

Figure 4:
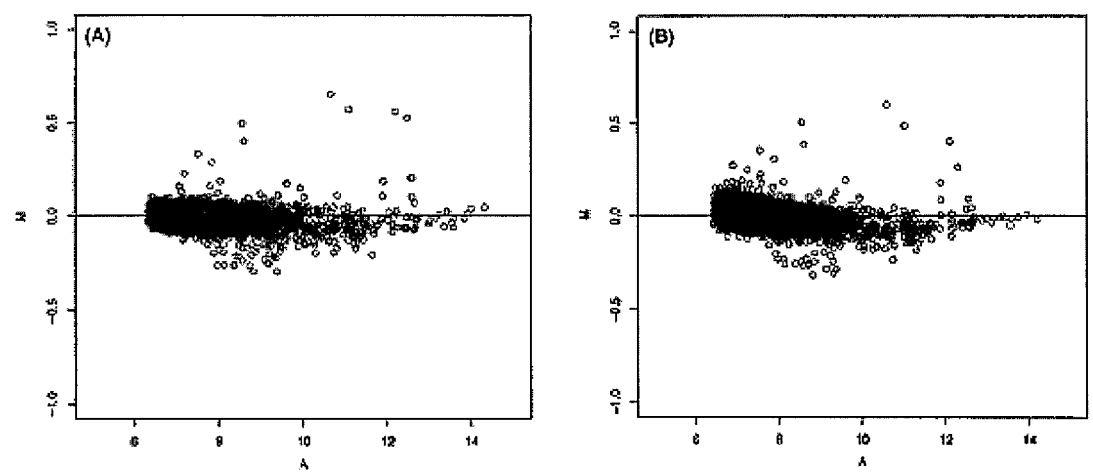
FIG. 4 shows the M-A plots of spike-in data after SUB-SUB normalization: (A) trimming fraction is 0.4; (B) trimming fraction is 0.

We carry out SUB-SUB normalization to each of the eight arrays using Array M as the reference. We experimented with different sub-array sizes, overlapping sizes and trimming fractions. FIG. 4 shows the M-A plots summarized from the eight arrays after normalization, namely, the log-ratios of expressions between the two groups versus the abundance. The sub-array size is 20·20, the overlapping size is 10 and the trimming factor are 0.4 and 0 in the subplots FIGS. 4A and B, respectively. Our result indicates that both the sub-array size (data not shown) and trimming fraction matter substantially for normalization. In other words, stratification by spatial neighborhood and selection of breakdown value in LTS do contribute a great deal to normalization. Overlapping size has a little contribution in this dataset. Our method identifies 14 of the 16 differentially expressed spike-in gene with only a few false positives (FIG. 4A).

Perturbed Spike-in Dataset

SUB-SUB normalization protects substantial differentiation by selecting an appropriate trimming fraction in LTS. To test this, we generate an artificial dataset with relatively large fraction of differentiation by perturbing the HG-U95 spike-in dataset. Namely, we randomly choose 20% genes and increase their corresponding probe intensities by 2.5-fold in the four arrays in the second group. We then run SUB-SUB normalization on the perturbed dataset with various trimming fractions. The results are shown in FIG. 3A, B, C, D for four trimming fractions, 50, 30, 20 and 10%. The normalization is satisfactory when the trimming fraction is >30%, or 10% larger than the nominal differentiation fraction. The extra fraction may account for random variation. In another case, we randomly choose 20% genes and increase their corresponding probe intensities by 1.5-fold. The results corresponding to the trimming fraction 50 and 0% are shown in FIGS. 3E and F respectively. We note that the black dots are blocked by red ones in these two subplots when they overlap.

Primate Brain Expression Dataset

Compared with other primate brains, such as chimpanzee and orangutan, a relatively high percentage of genes are differentially expressed in human brains, and most of them are upregulated in human brains (19,20). Moreover, the chimpanzee and orangutan samples are hybridized with human HG-U95 chips, so it is reasonable to assume if there were any measurement bias in primate mRNA expressions compared with humans, it would be a downward bias. FIG. 4A-D shows the density functions of log-ratios of gene expressions for four cases: HUMAN 1 versus ORANG.; HUMAN 2 versus ORANG.; HUMAN 1 versus CHIMP. 1; HUMAN 1 versus HUMAN 2. The results from SUB-SUB (trimming fraction is 20%) and quantile normalization are plotted in red and blue, respectively. When comparing humans with primates, the distribution resulted from the SUB-SUB method is to the right of that resulted from the quantile method. This is more obvious in the cases of humans versus orangutan, which are more genetically distant from each other than other cases do; see FIGS. 4E and F. As expected, the distributions skew to the right and the long tails on the right might have a strong influence on the quantile normalization, which aims to match marginal distributions from humans and primates in a global fashion. However, in the cases of HUMAN 1 versus ORANG. and HUMAN 2 versus ORANG., the modes corresponding to the quantile method are in the negative territory while the modes corresponding to SUB-SUB method are closer to zero. The results from SUB-SUB normalization seem to be more reasonable. Furthermore, the difference in the case of HUMAN 1 versus HUMAN 2 is more distinct than that in the case of HUMAN 1 versus CHIMP. 1; see the two subplots at the bottom. The analysis in (17) also indicates that HUMAN 2 differs more from other human samples than the latter differ from the chimpanzee samples. We checked the M-A plot of HUMAN2 versus ORANG after SUB-SUB normalization (figure not shown) and observed that HUMAN 2 has more up-regulated genes than down-regulated genes compared with ORANG.

Variation Reduction by Sub-array Normalization

Figure 5:
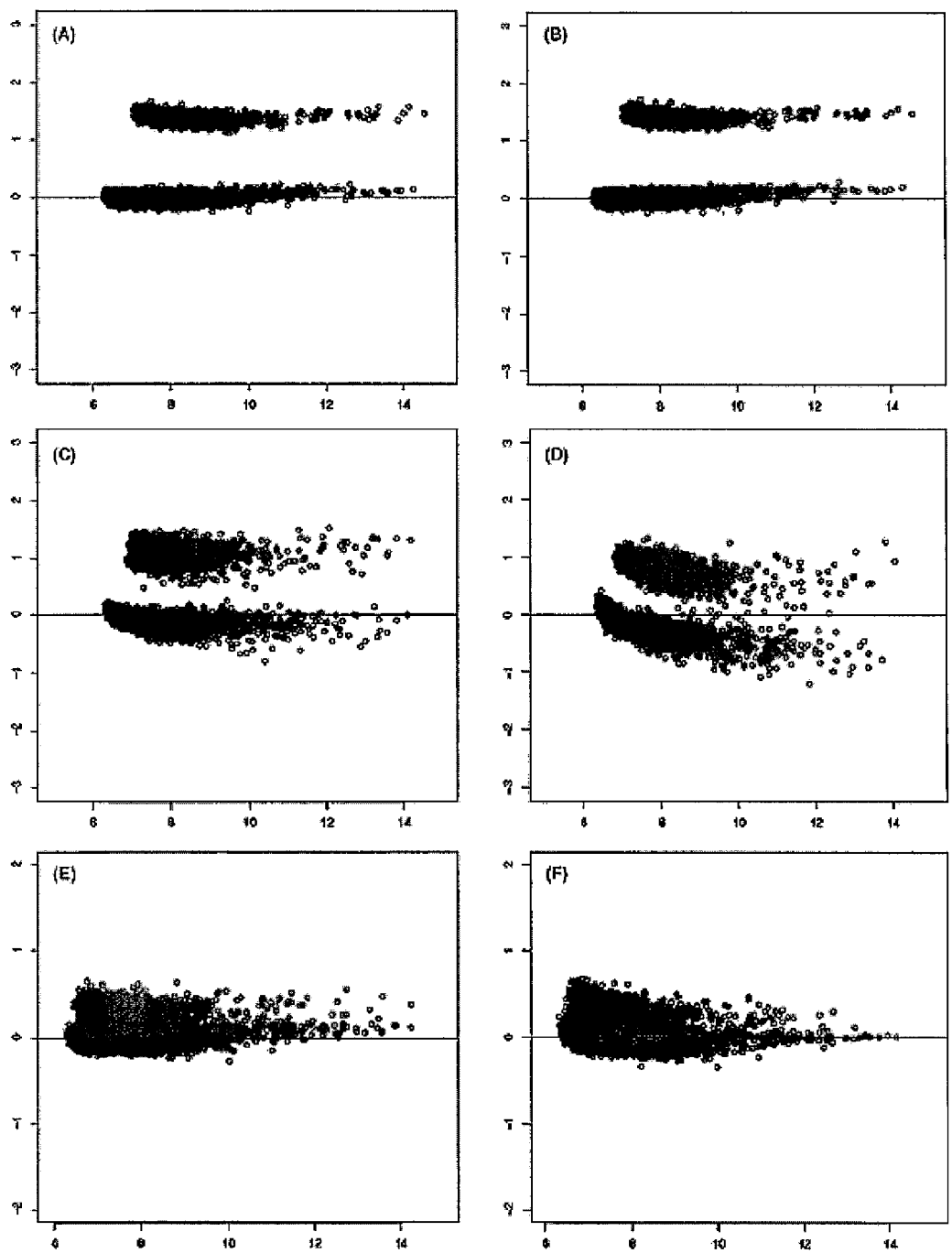
FIG. 5 (A-F)M-A plots of perturbed spike-in dataset after SUB-SUB normalization. The x-axis is the average of log-intensities from two arrays. The y-axis is their difference after normalization. In the top four subplots, 20% randomly selected genes have been artificially up-regulated by 2.5-fold in Array Q, R, S and T. The differentiated genes are marked red, and undifferentiated genes are marked black. The trimming fractions in the subplots are: A, 50%; B, 30%; C, 20%; D, 10%. In the two subplots at the bottom, 20% randomly selected genes have been artificially up-regulated by 1.5-fold in Array Q, R, S and T. The trimming fractions are: E, 50%; F, 0%.

Stratification is a statistical technique to reduce variation. Subarray normalization can be regarded as a way of stratification. We normalize the yeast array 2-121502 versus 2-121501 by various normalization methods available from Bioconductor. Since the two arrays are replicates, the difference between them is due to experimental variation. In the resulting M-A plots, we fit lowess curves to the absolute values of M, or |M|. These curves measure the variation between the two arrays after normalization (see FIG. 5). The sub-array normalization achieves the minimal variation. As variation is reduced, signal-to-noise ratio is enhanced and power of significance tests is increased.

Other normalization procedures can be applied at the sub-array level as well. For example, if differentiation is not substantial, we can apply quantile, lowess, qspline normalization, etc. We note that different statistical methods, especially those non-parametric ones, may have specific requirements on the sample size. To achieve statistical effectiveness, we need to select the size of sub-array for each normalization method.

Discussion

External Controls

In cDNA arrays, some designs use external RNA controls to monitor global messenger RNA changes. In our view, external RNA controls play the role of undifferentiated probe sets. To carry out local normalization, we need quite some number of external controls for each subgrid. In current Affymetrix arrays, this is not available. In the Affymetrix yeast2.0 arrays, probes for budding yeast, fission yeast, and some bacteria genes such as from *E. coli* are included. If the biological samples are from budding yeast, then we take probes from other organisms such as fission yeast and bacteria as controls. In normalization methods of the present invention, some embodiments may take only external control probes if they are available.

In many microarray experiments, our primary goal is the identification of differentially expressed genes. But the degree of differentiation may be quite different from one case to another. Next, we briefly mention some cases in which a large fraction of genes may be differentially expressed between two samples. First, in one study of the life span of yeast, we compare expression profiles of a wild-type strain with another, such as sch9D. The metabolism in the knock-out strain is greatly reduced and this leads to life span extension. Second, gene chips for some organisms are not available. Cross-species hybridization is a useful strategy for comparative functional genomics. The comparison of brain expressions of humans versus primates discussed earlier is one such example. Third, some customized arrays are so designed that only probes of hundreds of genes relating to a specific biological pathway are included for the consideration of cost. SUB-SUB normalization uses LTS to identify a 'base' subset of probes for adjusting difference in background and scale. In theory, the method can be applied to microarray experiments with differentiation fractions as high as 50%. In addition, our method does not assume an equal percentage of up- and down-regulated genes. In the mean time, LTS keeps the statistical efficiency advantage of least squares.

Nonlinear Array Transformation Versus Linear Sub-array Transformation

To eliminate the nonlinear phenomenon seen in M-A plots or Q-Q plots, methods such as lowess, qspline and quantile normalization use nonlinear transformation at the global level (6,7,22). In comparison, we apply a local strategy in SUB-SUB normalization. One array is split into sub-arrays and a simple linear transformation is fitted for each sub-array. With an appropriate sub-array size and trimming fraction, the nonlinear feature observed in M-A plots is effectively removed by linear sub-array transformation to a great extent. We hypothesize that the nonlinear phenomenon is partially caused by spatial variation. One simulation study also supports this hypothesis, but further investigation is required. Next, we give one remark regarding nonlinearity. In normalization, we adjust the intensities of a target array compared with those of a reference. Even though the dye effect is a nonlinear function of spot intensities, we show that a linear transformation is a good approximation as long as the majority of probe intensities from the target and reference are in the same range and thus have similar nonlinear effect. Occasionally when the amount of mRNA from two arrays is too different, slight nonlinear pattern is observed even after sub-array normalization. To fix the problem, we can apply global lowess after the sub-array normalization. Alternatively, to protect substantial differentiation, we can apply a global LTS normalization subject to a differentiation fraction once more.

Transformation

The variance stabilization technique was proposed in relation to normalization. We have tested SUB-SUB normalization on the log-scale of probe intensities, but the result is not as good as that obtained on the original scale. After normalization, a summarization procedure reports expression levels from probe intensities. we have tried the median polishing method (18) on the log-scale. Alternatively, we can do a similar job on the original scale using Model Based Expression Indexes (MBEI).

Usage of MM Probes

Figure 7:
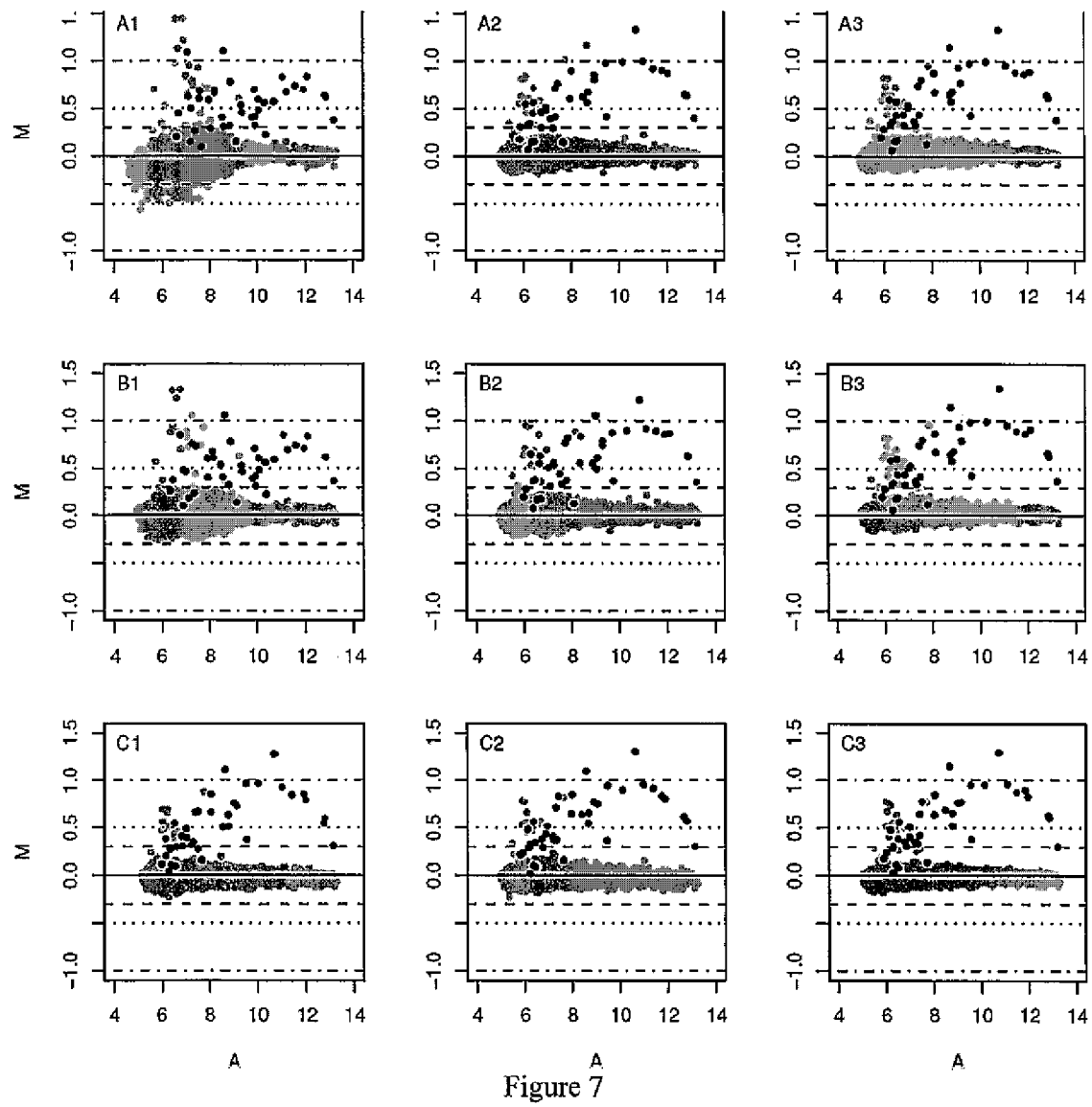
FIG. 7 Top (A1-A3): invariant-set; middle (B1-B3): quantile; bottom (C1-C3): sub-array. Left column (A1, B1 and C1): the reference is perturbed array Exp03 R1*; Middle column: the reference in both A2 and C2 is array Exp03 R2, while the reference in B2 is the pseudo-reference defined as the average quantiles of all six arrays; Right column (A3, B3 and C3): the PTR method result obtained using all six arrays as references. The grey dots are non-spike-in genes; the black dots are spike-in genes which are expected to have log-ratio M=1. We can see that PTR method results are not affected by the perturbed array Exp03 R1* and offers the smallest variation for non-spike-in genes.

Some studies suggested using PM probes only in Affymetrix chips. We checked the contribution of MM probes and PM probes to the subsets associated with LTS regressions from all subarrays. FIG. 7 shows the distribution of the percentage of MM probes in the subsets identified by LTS. Our result shows that MM probes contribute slightly more than PM probes in LTS regression, mostly in the range 46-56%.

Diagnosis

The detection of bad arrays is a practical problem in the routine data analysis of microarrays. In comparison with the obvious physical damages, such as bubbles and scratches, subtle abnormalities in hybridization, washing and optical noise are more difficult to detect. By checking values of a and b in LTS across sub-arrays, we can detect bad areas in an array and save information from the rest areas. Consequently, we can report partial hybridization result instead of throwing away an entire array.

Example 2

Microarray Data Sets

The Affymetrix HG-U133A data set contains triplicate of 14 experiments with 42 spike-in genes. These spike-in genes are organized into 14 gene groups, each of which contains 3 genes of the same concentration. The concentrations range from 0-512 pM according to a 14×14 Latin square design.

We analyze experiment 3 and 4 particularly. Experiment 3 contains triplicate: Exp03_R1, Exp03_R2 and Exp03_R3; experiment 4 contains triplecate: Exp04_R1, Exp04_R2 and Exp04_R3. The concentrations of 36 spike-in genes in experiment 4 are two-fold higher; the concentrations of the remaining 6 spike-in genes are 0 in either experiment 3 or 4. Later we refer to these six arrays as data set "Expt-3-4". Besides, we generate a perturbed data set by adding noise to array Exp03_R1 and keeping the other five arrays unchanged. The noise value is defined by $\delta_i = \max(0, x_i)$, where $x_i$ is a normally distributed random variable with a zero mean and variance equal to that of the array Exp03_R1. We denote this perturbed array by Exp03_R1.

We use another data set, the "Golden spike" data set of Choe et al. in 2005, to assess the detection power of differentially expressed genes. The data set contains six Affymetrix DrosGenomel chips, including three replicates for control and three for treatment. A total of 1309 genes are differentially expressed with pre-defined fold changes from the set, {1.2,1.5,1.7,2.0,2.5,3.0,3.5,4.0}, between the treatment and control.

Perturbed Data Set

Because the PTR method uses multiple references and the robust LAD implementation, we expect that the expression estimates are resistant to a single bad reference array. In FIG. 7, we show the M-A plots of the perturbed data set using different combinations of normalization and reference selections. In these M-A plots, M values are the log-ratios of experiment 4 versus experiment 3 for all probe-sets and the A values are the average log-intensities of the two experiments.

The top, middle, and bottom rows show the results from the invariant-set, quantile, and sub-array normalization respectively. In A1-B1-C1, we take the perturbed array Ep03_R1* as the reference; in A2-C2, we take the array Exp03_R2 as the reference, while in B2, we take the average quantiles as the pseudo-reference; in A3-B3-C3, we simply use the PTR method coupled with the reference set of all six arrays. We see that the invariant-set is more sensitive to the perturbed reference array Exp03 R1* (A1) and it performs well if an appropriate reference is selected (A2). The quantile method shows a similar but less severe phenomenon when the quantile-quantile transformation is based on the array Exp03_R1* In contrast, the quantile normalization using average quintiles as the pseudo-reference is more resistant to this perturbation. For the sub-array normalization, the perturbation does not affect the ratio estimates, since the normalization transformations are done in each sub-window which greatly reduce the effects of this global noise.

The PTR method improves the results in all three normalization algorithms. We see that the log-ratios of spike-in genes are more close to the expected log-ratio value M=1 and, and non-spike-in genes have smaller variations along M=0. The PTR method deals with the single perturbed reference array Exp03_R1 well, and it estimates the final transcript abundance robustly.

Variation Reduction by the PTR Method

We see that the PTR method achieves smaller variances for the non-spike-in genes in the M-A plots of the perturbed data set. To measure the effectiveness of the PTR method in variation reduction, we compare it with other pre-processing methods using "Expt-3-4" data set. The non-spike-in genes are expected to have the same expression in both experiment 3 and 4, and the differences between them are due to the non-biological factors. We preprocess six arrays with different methods of normalization and summarization and estimate the expression values for both experiment 3 and 4. In the M-A plots, we fit loess curves to the absolute values of M against A using non-spike-in genes only. The result curves shown in FIG. 8 measure the variations of non-spike-in genes between two experiments. The left, middle, and right column show the results from the invariant-set, quantile, and sub-array normalization method respectively. Except for the PTR method, we summarize the normalized results using the expresso function in the affy package with either the Li-Wong's MBEI or the median polish method. From the plots, we can see that the PTR method achieves the smallest variations for each normalization algorithm.

In the left plot, we use the invariant-set normalization for both the PTR method and the other single-reference methods. The plot shows that the same pre-processing method but with different reference choices results in different variation curves. The PTR method reduces the background noise significantly.

In the middle plot, we use the quantile normalization, taking each raw array as well as the average quantiles to be the reference. The plot shows substantial improvement by the PTR method, while the quantiles normalization achieves a moderate performance using the average quantiles as the pseudo-reference. The PTR method gives a better strategy to use the complete data information.

Figure 8:
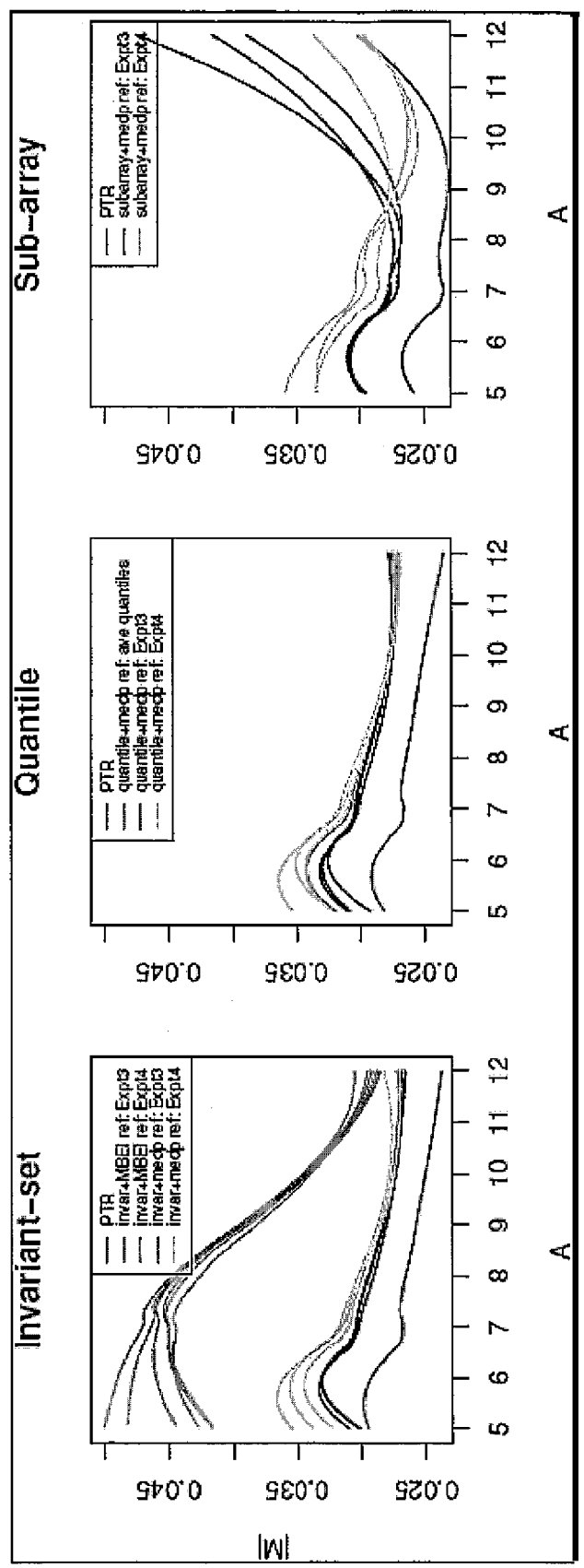
FIG. 8 These plots compare the PTR method with other pre-processing methods based on the variation of non-spike-in genes. The PTR method gives the smallest variation for all three normalization algorithms.

In the right plot of FIG. 8, we use the sub-array normalization, and the plot shows the improvement by the PTR method once again. Furthermore, we clearly see two different types of curves from the single-reference results. Each reference array from experiment 3 performs better at the low intensity range but worse in the high intensity range; whereas each from experiment 4 performs slightly better in the high intensity range but worse in the low intensity range. A similar yet less prominent pattern also exists in the results using the invariant-set and quantile normalization. Replicates within either experiment 3 or 4 are similar, but arrays from two experiments lead to more different results. The PTR method takes into account reference arrays from both experiments, combines two types of expression results and gives the smallest variation in both low and high intensity ranges.

The loess assessment has demonstrated that the PTR method can reduced the variation significantly for the invariant-set, quantile and sub-array normalization method. This variation reduction, especially in the low intensity range, is particularly valuable in the measurement of gene expressions.

Improvement on Detection of Differentially Expressed Genes

Figure 9:
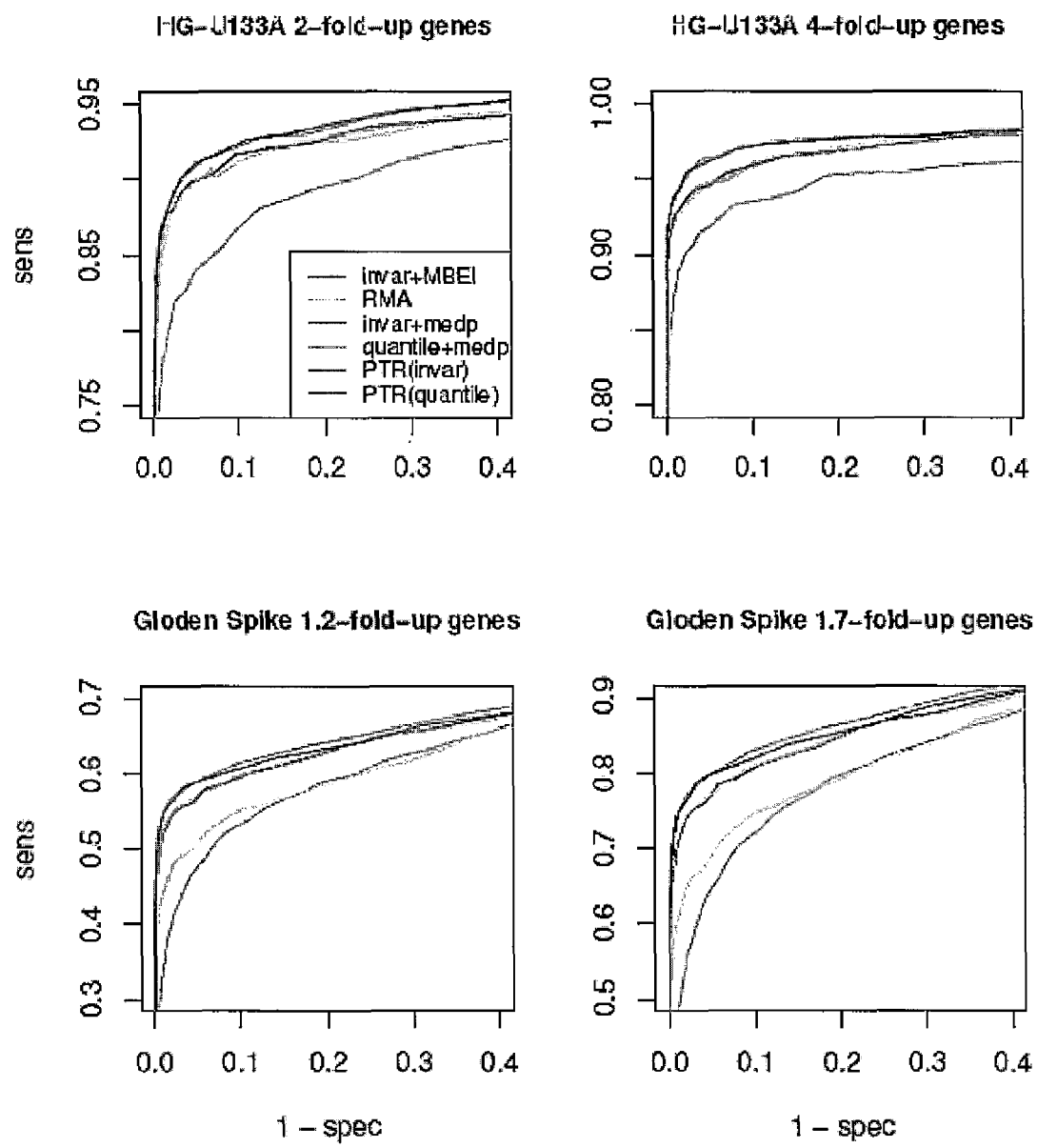
FIG. 9 X-axis: 1—specificity; Y-axis: sensitivity. The PTR method performs the best in all cases.

In order to ensure that deferential gene detection is not sacrificed in the effort to reduce the variation by the PTR method in expression analysis, we compute the receiver operating characteristic (ROC) curves using the HG-U133A data set. We conduct two comparative studies on this data set. In the first study, we compare every two experiments which are next to each other in the Latin square design. Each pair of experiments have 36 spike-in genes with 2-fold change. In the second study, we compare every two experiments which are separated by one and exactly one experiment. Each pair of experiments have 36 spike-in genes with 4-fold change. In total, we have 14 pairs of experiments in each study. The curves computed by the ROC package from Bioconductor are shown at the top of FIG. 9. We compare the PTR method with various pre-processing combinations in the expresso function of the affy package, which includes: invariant-set normalization plus Li-Wong's MBEI or median polish summarization; quantile normalization plus median polish summarization with or without RMAs background correction. We see that the PTR method does equally well with both the quantile and invariant-set normalization algorithm in this data set. The PTR method gives the best performance in the detection of the differentially expressed genes.

In addition, we make the similar comparisons on the "golden spike" data set. We set the differentially expressed genes using fold change threshold to 1.2 or 1.7. The ROC curves are shown at the bottom of the FIG. 9. We can see that the PTR method performs better with the invariant-set normalization than the quantile normalization method. However, both of them outperform the other pre-processing methods.

The assessment on both data sets demonstrates that the PTR method provides higher specificity and sensitivity. The noise reduction improves the detection of deferentially expressed genes.

Discussion

We explicitly address the reference issue in pre-processing expression microarray and propose the PTR method to carry out the normalization and summarization jointly. The PTR method can be applied to existing normalization methods, including the invariant-set, sub-array, and quantile. It is the first time we propose a practical scheme to implement the sub-array normalization. The sub-array takes into account the spatial pattern of hybridization, and can properly normalize the majority of probe intensities even in the presence of scratches or serious non-homogeneous hybridization. The PTR method enhances this ability using multiple references in the normalization and implicitly selecting a "reference" at the probe-set level during summarization.

In this Example, we have discussed the experiment design with replicates. Special attention needs to be paid when an experiment has no replicates. We have not discussed the background correction issue, but the existing background correction methods can be implemented before the normalization step of the PTR method. Interestingly, we have shown that the PTR method reduces the variation of non-differentially expressed genes, especially in the low intensity range. As a consequence, we improve the signal-to-noise ratio, and we increase the detection power of the deferentially expressed genes. The improvement is achieved without any additional information.

Figure 11:
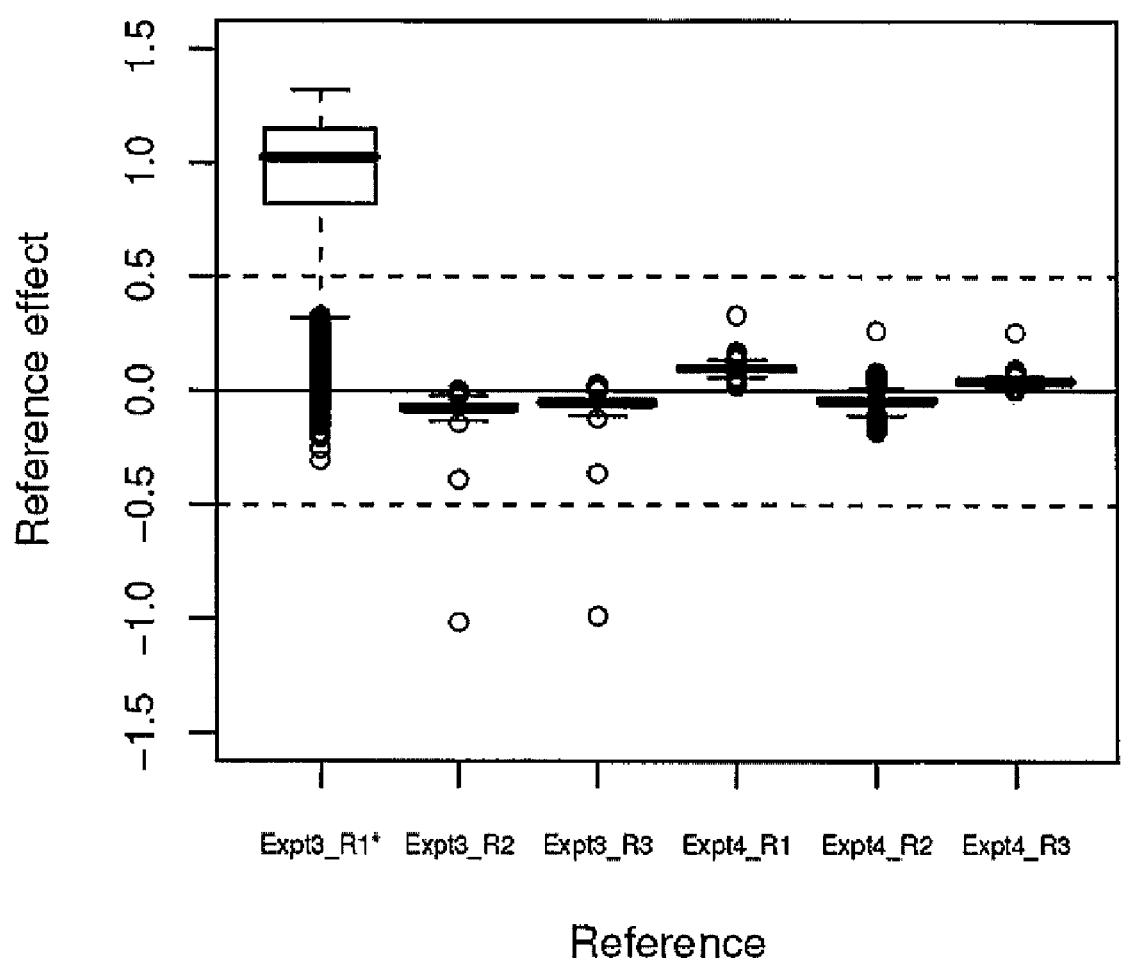
FIG. 11 This reference effect box plot is get from the PTR model fitting on the perturbed data set after the invariant-set normalization. The first reference array, Exp03 R1*, has been perturbed by adding noise. It shows a quite different distribution than others.

We include all arrays in the reference set and use the cross strategy to select the corresponding target arrays in this paper. We are aware that they may not be the optimal strategy for reference and target selection. However, the PTR method can protect against and detect abnormal arrays. First, by using the robust LAD method in the summarization, we can accurately estimate the transcript abundance as long as the majority of normalization results are right. Second, we can evaluate the array quality by the reference effect distribution, as shown in FIG. 11. The array showing distinct distribution from other arrays is likely a bad candidate for reference and may be excluded from the reference set in the next-round PTR processing.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A computer implemented method of analyzing data obtained from a plurality of microarrays, wherein said data are arranged in the form of data grids corresponding to the respective physical grids of the microarrays from which the data were obtained, said method comprising the steps of:

inputting said microarray data to a processing unit configured to perform the steps of:

selecting a first microarray and a second microarray for comparison;

normalizing, pairwise, the second microarray against the first microarray by preforming the following steps:

dividing data from each of the two microarrays into equal number of subarrays of a predetermined size, wherein said subarrays either do not overlap or overlap with adjacent subarrays by a predetermined overlap percentage;

estimating a linear relationship between a subarray of the first microarray and a corresponding subarray of the second microarray by applying a least trimmed squares regression method with a predetermined trimming fraction;

transforming data in the corresponding subarray of the second microarray by applying the estimated linear relationship;

applying the estimating and transforming steps to the remaining subarrays until all subarrays in the second microarray have been transformed; and outputting the transformed values of the second microarray as normalized microarray data of the second microarray against the first microarray.

2. The method of claim 1, wherein the microarray is one selected from the group consisting of oligonucleotide arrays, cDNA arrays, bead arrays, pathway arrays, ChIP-chip experiments, methylation arrays, exon array, tissue arrays and protein arrays.

3. The method according to claim 2, wherein the microarray is an oligonucleotide array and wherein all data points from the oligonucleotide array are used in the normalizing step.

4. The method according to claim 1, wherein a set of multiple target-reference pairs of microarrays are selected from raw microarray data, and wherein the pairwise normalization step is performed to output normalized target microarray data for each target-reference pair in the set.

5. The method of claim 1, wherein said first and second microarrays contain data from probes that are differentiated, and the least trimmed squares method uses a trimming fraction larger than the fraction of differentiated probes.

6. The method of claim 1, wherein each subarray independently has a size of from about 10×10 data points to a size smaller than the whole array.

7. A computer readable medium having encoded thereon instructions to direct a computer to perform a method of analyzing microarray data, said method comprising the steps of:

receiving data obtained from a plurality of microarrays;

selecting data from a first microarray and a second microarray for pairwise comparison;

dividing data from said first and second microarrays into equal number of corresponding subarrays with a predetermined subarray size, wherein said subarrays either overlap with adjacent subarrays by a predetermined overlap percentage or do not overlap with adjacent subarrays;

estimating a linear relationship between a subarray from the first microarray and a corresponding subarray from the second microarray by applying a least trimmed squares regression method with a predetermined trimming fraction;

transforming the data of the subarray from the second microarray by applying the estimated linear relationship;

repeating the estimating and transforming steps to all remaining subarrays; and outputting the transformed data of the second microarray as a pairwise normalized data against the first microarray for further analysis.

8. The computer readable medium of claim 7, wherein said method further comprises the step of averaging the values of data within the overlapped region of the subarrays.

9. The computer readable medium of claim 7, wherein said method further comprises the steps of:

taking one or more of the pairwise normalized data as input;

generating a summary statistics by comparing the pairwise normalized data of the second microarray to the data of the first microarray.

10. The computer readable medium of claim 7, wherein said microarray data represent amount of gene expressions in one or more biological samples, and said summary statistics is one or more gene expression profiles of the biological samples determined by comparing against multiple reference arrays using a three-factor model that accounts for probe effect, treatment effect, and reference effect.

11. The method of claim 1, wherein said processing unit is configured to perform the further step of averaging the values of data within the overlapped region of the subarrays.

12. The method of claim 1, wherein said processing unit is configured to perform the further steps:

taking one or more of the normalized data obtained from the pairwise normalization as input;

generating a summary statistics by comparing the pairwise normalized data of the second microarray to the data of the first microarray.

13. The method of claim 1, wherein said microarray data represent amount of gene expressions in one or more biological samples, and said summary statistics is one or more gene expression profiles of the biological samples determined using a three-factor model that accounts for probe effect, treatment effect, and reference effect.

14. A computer system for analyzing microarray data, comprising:

a data receiving unit for receiving data obtained from a plurality of microarrays; and a processing unit configured to perform the steps of selecting a first microarray and a second microarray for comparison;

normalizing, pairwise, the second microarray against the first microarray by preforming the following steps:

dividing data from each of the two microarrays into equal number of subarrays of a predetermined size, wherein said subarrays either overlap with adjacent subarrays by a predetermined overlap percentage or do not overlap with adjacent subarrays;

estimating a linear relationship between a subarray of the first microarray and a corresponding subarray of the second microarray by applying a least trimmed squares regression method with a predetermined trimming fraction;

transforming data in the corresponding subarray of the second microarray by applying the estimated linear relationship;

applying the estimating and transforming steps to the remaining subarrays until all subarrays in the second microarray have been transformed; and outputting the transformed values of the second microarray as normalized microarray data of the second microarray against the first microarray.

15. The computer system of claim 14, wherein said processing unit is configured to perform the further step of averaging the values of data within the overlapped region of the subarrays.

16. The computer system of claim 14, wherein said processing unit is configured to perform the further steps of:

taking one or more of the normalized data from the pairwise normalization as input;

generating a summary statistics by comparing the pairwise normalized data of the second microarray to the data of the first microarray.

17. The computer system of claim 14, wherein said microarray data represent amount of gene expressions in one or more biological samples, and said summary statistics is one or more gene expression profiles of said biological samples determined by comparing against multiple reference arrays using a three-factor model that accounts for probe effect, treatment effect, and reference effect.

* * * * *